(12) United States Patent
Enoki et al.

(10) Patent No.: US 10,214,769 B2
(45) Date of Patent: Feb. 26, 2019

(54) METHOD FOR DESIGNING PROBE IN DNA MICROARRAY, AND DNA MICROARRAY PROVIDED WITH PROBE DESIGNED THEREBY

(71) Applicant: TOYOTA JIDOSHA KABUSHIKI KAISHA, Toyota-shi, Aichi (JP)

(72) Inventors: Hiroyuki Enoki, Okazaki (JP); Satoru Nishimura, Nagoya (JP); Aya Murakami, Hoi-gun (JP)

(73) Assignee: TOYOTA JIDOSHA KABUSHIKI KAISHA, Toyota-shi, Aichi (JP)

( * ) Notice: Subject to any disclaimer, the term of this patent is extended or adjusted under 35 U.S.C. 154(b) by 33 days.

(21) Appl. No.: 15/445,262

(22) Filed: Feb. 28, 2017

(65) Prior Publication Data

US 2017/0166951 A1 Jun. 15, 2017

Related U.S. Application Data

(62) Division of application No. 13/499,618, filed as application No. PCT/JP2010/072322 on Dec. 13, 2010, now abandoned.

(30) Foreign Application Priority Data

Dec. 14, 2009 (JP) .................................. 2009-283430

(51) Int. Cl.
| | |
|---|---|
| *C12Q 1/683* | (2018.01) |
| *C12Q 1/6837* | (2018.01) |
| *C12Q 1/6809* | (2018.01) |
| *C12Q 1/6855* | (2018.01) |
| *C12Q 1/6806* | (2018.01) |

(52) U.S. Cl.
CPC .......... *C12Q 1/683* (2013.01); *C12Q 1/6806* (2013.01); *C12Q 1/6809* (2013.01); *C12Q 1/6837* (2013.01); *C12Q 1/6855* (2013.01)

(58) Field of Classification Search
CPC ..... C12Q 1/683; C12Q 1/6806; B01J 19/0046
See application file for complete search history.

(56) References Cited

U.S. PATENT DOCUMENTS

| | | | |
|---|---|---|---|
| 6,361,947 B1 | 3/2002 | Dong et al. | |
| 6,713,258 B2 | 3/2004 | Kilian | |
| 6,958,225 B2 | 10/2005 | Dong | |
| 2003/0044791 A1 | 3/2003 | Flemington | |
| 2003/0162181 A1 | 8/2003 | Yang et al. | |
| 2005/0164198 A1 | 7/2005 | Imai et al. | |
| 2005/0208513 A1 | 9/2005 | Agbo et al. | |
| 2007/0016382 A1 | 1/2007 | Webster et al. | |
| 2007/0054272 A1 | 3/2007 | Brachet et al. | |
| 2008/0187912 A1 | 8/2008 | Petersdorf et al. | |
| 2009/0036323 A1 | 2/2009 | Wan Eijk et al. | |
| 2009/0118136 A1 | 5/2009 | Deng | |
| 2009/0269749 A1 | 10/2009 | Van Eijk et al. | |
| 2009/0318304 A1 | 12/2009 | Drmanac et al. | |

FOREIGN PATENT DOCUMENTS

| | | |
|---|---|---|
| CN | 1995384 | 7/2007 |
| CN | 101310024 | 11/2008 |
| CN | 101343667 | 1/2009 |
| CN | 101381724 | 3/2009 |
| CN | 101550434 | 10/2009 |
| JP | 2002532070 | 10/2002 |
| WO | 0034518 | 6/2000 |
| WO | 2007055568 | 5/2007 |

OTHER PUBLICATIONS

Wittenberg et al., "Validation of the high-throughput marker technology DArT using the model plant *Arabidopsis thaliana*," Mol. Gen. Genomics, 274(1):30-39 (2005).

Jaccoud et al., "Diversity arrays: a solid state technology for sequence information independent genotyping," Nucleic Acids Research, 29(4):1-7 (2001).

Mace et al., "A consensus genetic map of sorghum that integrates multiple component maps and high-throughput Diversity Array Technology (DArT) markers," BMC Plant Biology, 9(13):1-14 (2009).

International Search Report of PCT/JP2010/072322, dated Feb. 15, 2011.

Office Action issued in corresponding Chinese Patent Application No. 201080063662.3 dated Mar. 29, 2013.

Akbari et al., "Diversity arrays technology (DArT) for high-throughput profiling of the hexaploid wheat genome", Theor. Appl. Genet., 113(8):1409-1420 (2006).

Tinker et al., "New DArT markers for oat provide enhanced map coverage and global germplasm characterization", BMC Genomics, 10(39):1-22 (2009).

Wenzl et al., "A DArT platform for quantitative bulked segregant analysis," BMC Genomics, 8(196):1-10 (2007).

Wenzl et al., "Diversity Arrays Technology (DArT) for whole-genome profiling of barley" PNAS, 101(26):9915-9920 (2004).

Tuberosa et al., "The fast and the cheap: SNP and DArT-based whole genome profiling for crop improvement" In the Wake of the Double Helix: From the Green Revolution to the Gene Revolution, pp. 443-461 (Sep. 2005).

Office Action, dated Sep. 6, 2012, issued by the USPTO in U.S. Appl. No. 13/499,618.

Non-Final Office Action, dated Dec. 21, 2012, issued by the USPTO in U.S. Appl. No. 13/499,618.

(Continued)

*Primary Examiner* — Narayan K Bhat
(74) *Attorney, Agent, or Firm* — Sughrue Mion, PLLC

(57) ABSTRACT

Provided is a probe to be used in a DNA microarray having an excellent detection rate of a polymorphism such as SNP contained in genomic DNA. A method for designing a probe according to the invention includes the steps of: specifying one or more regions covering at least a part of fragments flanked by restriction enzyme recognition sites recognized by a restriction enzyme, contained in genomic DNA derived from an organism to be tested; and designing a probe for the specified one or more regions for detecting the fragment in the organism to be tested.

5 Claims, 9 Drawing Sheets
Specification includes a Sequence Listing.

(56) References Cited

OTHER PUBLICATIONS

Final Office Action, dated Aug. 1, 2013, issued by the USPTO in U.S. Appl. No. 13/499,618.
Advisory Action, dated Nov. 7, 2013, issued by the USPTO in U.S. Appl. No. 13/499,618.
Non-Final Office Action, dated Sep. 9, 2014, issued by the USPTO in U.S. Appl. No. 13/499,618.
Final Office Action, dated Feb. 3, 2015, issued by the USPTO in U.S. Appl. No. 13/499,618.
Advisory Action, dated Jun. 9, 2015, issued by the USPTO in U.S. Appl. No. 13/499,618.
Non-Final Office Action, dated Aug. 7, 2015, issued by the USPTO in U.S. Appl. No. 13/499,618.
Final Office Action, dated Jan. 8, 2016, issued by the USPTO in U.S. Appl. No. 13/499,618.
Advisory Action, dated Apr. 13, 2016, issued by the USPTO in U.S. Appl. No. 13/499,618.
Non-Final Office Action, dated Jun. 29, 2016, issued by the USPTO in U.S. Appl. No. 13/499,618.
Final Office Action, dated Nov. 30, 2016, issued by the USPTO in U.S. Appl. No. 13/499,618.

Figure 5

```
A_1      1:AATACCCCTCTCTAGGCTTTGGAATTGTGCTGTGATGATAAAATGAATGTGATGCAAATG 60
A_2      1:AATATCTGG--------------------------------------------------- 9
           **** *

Probe PA_1 :AATACCCCTCTCTAGGCTTTGGAATTGTGCTGTGATGATAAAATGAATGTGATGCAAATG
Probe PA_2 :                                                   GATGCAAATG A_1     61:CTCATGCTTTGGAATTAGAGCCTTTCAGTCCTGAGCTAGGTAGGCTTTACTAGCTGTTAT 120
A_2     10:----------------GAGCCTTTCAGTCCTGAGCTAGGTAGGCTTTACTAGCTGTTAT 52
                          ********************************************

Probe PA_2 :CTCATGCTTTGGAATTAGAGCCTTTCAGTCCTGAGCTAGG
Probe PA_3 :                                        TAGGCTTTACTAGCTGTTAT A_1    121:TGTTTCTTTCCTATTGCTTATTTCGAGACCAGTATCCCTAAGAGTGGCATTTTTTTTCTG 180
A_2     53:TGTTTCTTTCCTATTGCTTATTTCGAGACCAGTATCCCTAAGAGTGGCATTTTTTTGCTG 112
           ************************************************************ ***

Probe PA_3 :TGTTTCTTTCCTATTGCTTATTTCGAGACCAGTATCCCTA
Probe PA_4 :                                        AGTATCCCTAAGAGTGGCATTTTTTTGCTG A_1    181:CCCCTAAGAGAGTACATTCATGTGTCTTGTGATGTAACAAATCACGTGTTCCTTCGCTAA 240
A_2    113:CCCCTAAGAGAGCACATTCATGTGTCTTGTGATGTAACAAATCACGTGTTCCTTCGCTAA 172
           ************ ***********************************************

Probe PA_4 :CCCCTAAGAGAGTACATTCATGTGTCTT
Probe PA_5 :                    GTGTCTTGTGATGTAACAAATCACGTGTTCCTTCGCTAA A_1    241:AATAAATATGCATGGTCCTC                                        260
A_2    173:AATAAATATGCATGGTCCTC                                        192
           ********************

Probe PA_5 :AATAAATATGCATGGTCCTC
```

Figure 6

```
B_1       1:ACCCGTTATTATCATATGTTTACTGTAGCACAATATTGTCTAATTACGGACTGATTAGGC 60
B_2       1:ACCTGTTATTATCATATGTTTACTGTAGCACAACATTGTCTAATTACGGACTAATTAGGC 60
            *** ***************************** ****************** ******

Probe PB_1 :ACCCGTTATTATCATATGTTTACTGTAGCACAATATTGTCTAATTACGGACTGATTAGGC
Probe PB_2 :                                                   CTGATTAGGC B_1      61:TCAAAAAAATCATCTCGCAAAATATACGCAATTTGTGTAATTAATTA-TTTTTTAGTCTA 119
B_2      61:TCAAAAAATCGTCTAGCAAAATACACGCAATCTGTGCAATTAATTATTTTTTTAGTCTA 120
            ********** *** ******* ******** **** **** ***** ***********

Probe PB_1 :TCAAAAAAT
Probe PB_2 :TCAAAAAAATCATCTCGCAAAATATACGCAATTTGTGTAATTAATTATTTTTTAGTCTA
Probe PB_3 :                                            TTAATTATTTTTTTAGTCTA B_1     120:CATTTAATACTTCATATGTGTGTCAAACATCCGATGTGATAGGGTAGGGGAGAAACTAA- 178
B_2     121:CATTTAATACTTCATACGTGTATCAAACATCCGATGTGATAGGGTAGAGGAGGAACTAAA 180
            **************** **** ************************* **** ******

Probe PB_3 :CATTTAATACTTCATATGTGTGTCAAACATCCGATGTGATAGGGTAGGGGA
Probe PB_4 :                                         GTGATAGGGTAGGGGAGAAACTAA B_1     179:-AAGTCC--------CACCATTATTTCGTACCAGTGAAGCTGACGCATCTTAATTGCTTC 229
B_2     181:CAAGTCCTTAGTTGCCAGCATTATTTCGTACCAGTGAAGCTGATGCATCTTAATTGCTTC 240
            ******          **  ************************* *************

Probe PB_4 : AAGTCC        CACCATTATTTCGTAC
Probe PB_5 :                                  CAGTGAAGCTGACGCATCTTAATTGCTTC B_1     230:TGACCAAATGTTTAGTAGCAGCAGTACTATCATATTCTTCCTGCTGCTCATAATATGATT 289
B_2     241:TGACCAAATGTTTAGTAGCAGCAGTACTATCATATTCTTCCTGCTACTCATAATATGATT 300
            ********************************************* *************

Probe PB_5 :TGACCAAATGTTTAGTAGCAGCA
Probe PB_6 :                       CAGTACTATCATATTCTTCCTGCTGCTCATAATATGATT B_1     290:TTGTCTTGCATATTTTCAGGAGACTACTGAG                              320
B_2     301:TTGTCTTGCATATTTTCAGGAGACTACTGAG                              331
            *******************************

Probe PB_6 :TTGTCTTGCATATTTTCAGGAGACTACTGAG
```

METHOD FOR DESIGNING PROBE IN DNA MICROARRAY, AND DNA MICROARRAY PROVIDED WITH PROBE DESIGNED THEREBY

CROSS REFERENCE TO RELATED APPLICATIONS

This application is a Divisional of U.S. application Ser. No. 13/499,618, filed Mar. 30, 2014; which is a National Stage of International Application No. PCT/JP2010/072322 filed Dec. 13, 2010; claiming priority based on Japanese Patent Application No. 2009-283430 filed Dec. 14, 2009; the contents of all of which are incorporated herein by reference in their entirety.

TECHNICAL FIELD

The present invention relates to a method for designing a probe used in a DNA microarray for detecting, for example, a mutation in genomic DNA, a DNA microarray having a probe designed by the method, and a method for detecting a mutation using the DNA microarray.

BACKGROUND ART

Of the polymorphisms represented by a single nucleotide polymorphism (SNP), there is a polymorphism that can be used as a mutation characterizing a variation in a homogenous organism. More specifically, a predetermined variation in a homogenous organism can be distinguished from other variations by detecting and identifying a specific mutation such as a polymorphism in genomic DNA. Furthermore, a variation of an organism to be tested can be specified by detecting and identifying the mutation.

As a method for detecting such a mutation in genomic DNA, a method of directly determining a sequence of a mutation site, a method of using a restriction enzyme fragment length polymorphism (RFLP), a method of using an amplification fragment length polymorphism (AFLP) and the like are known. In addition, a method of analyzing a variation based on identification of a polymorphism using a DNA microarray called as a DArT (Diversity Array Technology) method (Nucleic Acids Research, 2001, Vol. 29, No. 4, e25) is known.

A method for preparing a DNA microarray for use in the DArT method is shown in FIG. 9. First, genomic DNA is extracted from a predetermined organism species and fractionated with restriction enzyme A and restriction enzyme B. Next, to the both ends of each of the genomic DNA fragments obtained by the restriction enzyme treatment, an adaptor is connected and each of the genomic DNA fragments is cloned into a vector. Next, using a primer capable of hybridizing with the adaptor, genomic DNA fragments are amplified by PCR. Then, genomic DNA fragments amplified are spotted on a substrate as a probe to prepare a DNA microarray.

Using the DNA microarray thus prepared, a variation of a organism species to be tested can be analyzed. First, genomic DNA is extracted from an organism to be tested, and fractionated with restriction enzyme A and restriction enzyme B that are used for preparing the DNA microarray. To the genomic DNA fragments, an adaptor is connected similarly in the preparation of the DNA microarray and the resultant fragments are amplified by PCR. The amplified genomic DNA fragments are tagged with a fluorescent label etc. and hybridized with the probe spotted on the DNA microarray. Based on the presence or absence of hybridization of the labeled genomic DNA fragment with the probe detected, a difference between the predetermined organism species used in preparation of the DNA microarray and the organism species to be tested can be analyzed.

SUMMARY OF INVENTION

Technical Problem

According to the DArT method, the diversity of an organism species can be determined in a genotype level in the genomic DNA by using the DNA microarray prepared as mentioned above. However, the DNA microarray prepared as mentioned above has a problem in that the detection ability of a probe, which is defined as a region flanked by restriction enzyme recognition sites, is not sufficient. More specifically, even if a genomic DNA fragment derived from an organism species to be tested contains a small mutation such as SNP, the genomic DNA fragment may often hybridize with the probe of the DNA microarray. In other words, the DArT method has a detection limit, that is, detection cannot be made unless a mutation such as a polymorphism is present in a restriction enzyme recognition site or deletion of several hundreds of base pairs is present.

Then, in the aforementioned circumstances, the present invention is directed to providing a method for designing a probe of a DNA microarray having an excellent detection rate of a polymorphism such as SNP contained in genomic DNA, a DNA microarray having a probe designed by the method and a method for detecting a mutation using the DNA microarray.

Solution to Problem

In the aforementioned circumstances, the present inventors have made intensive studies and conceived a method for designing a probe capable of detecting even a small mutation such as SNP in the genomic DNA with an excellent sensitivity, and a method of detecting a mutation by using a DNA microarray having the probe immobilized thereto.

The present invention includes the followings.

More specifically, the method for designing a probe according to the present invention including the steps of: specifying one or more regions having a shorter nucleotide length than fragments flanked by restriction enzyme recognition sites recognized by a restriction enzyme, contained in genomic DNA derived from a target organism, and covering at least one portion of the genomic DNA fragments; and designing the specified one or more regions as a probe for detecting the fragment in an organism to be tested.

The one or more regions can be specified by performing the following steps:

(1a) extracting the genomic DNA;

(1b) digesting the extracted genomic DNA with the restriction enzyme;

(1c) connecting an adaptor to the genomic DNA fragments obtained the step (1b);

(1d) amplifying the genomic DNA fragments using a primer capable of hybridizing to the adaptor;

(1e) sequencing the amplified genomic DNA fragment; and (1f) determining the one or more regions based on the nucleotide sequence.

In the step (1b) herein, the genomic DNA may be digested with one or more restriction enzymes. Furthermore, in the step (1c), the adaptor used preferably has a complementary sequence to a protruding end of the genomic DNA fragments obtained the step (1b). Moreover, the region to be determined in the step (1f) has, for example, a 20 to 10000 nucleotide length, preferably, a 100 to 8000 nucleotide length and more preferably, a 200 to 6000 nucleotide length.

Furthermore, the one or more regions can be specified using nucleotide sequence data on the genomic DNA by performing the following steps:

(2a) searching the nucleotide sequence data on the genomic DNA for the restriction enzyme recognition sequence to specify the nucleotide sequence of the genomic DNA fragments obtained by digesting the genomic DNA with the restriction enzyme; and (2b) determining the one or more regions based on the specified nucleotide sequence.

Herein, the region determined in the step (2b) has, for example, a 20 to 10000 nucleotide length, preferably, a 100 to 8000 nucleotide length, and more preferably, a 200 to 6000 nucleotide length.

Furthermore, the one or more regions can be determined by performing the following steps:

(3a) extracting the genomic DNA;

(3b) digesting the extracted genomic DNA with the restriction enzyme;

(3c) connecting an adaptor to the genomic DNA fragments obtained in the step (3b);

(3d) amplifying the genomic DNA fragments using a primer capable of hybridizing to the adaptor;

(3e) digesting the amplified genomic DNA fragment with another restriction enzyme; and (3f) separating the DNA fragments obtained by digestion in the step (3e) as probes.

Furthermore, in the method for designing a probe according to the present invention, a fragment flanked by the restriction enzyme recognition sites may be a fragment flanked by more than one restriction enzyme having different recognition sequences.

In the step (3b) herein, the genomic DNA may be digested with one or more restriction enzymes. Furthermore, in the step (3c), the adaptor used preferably has a complementary sequence to a protruding end of the genomic DNA fragment obtained the step (1b).

On the other hand, the DNA microarray according to the present invention is prepared by immobilizing a probe designed by the aforementioned method for designing a probe according to the present invention on a carrier. Particularly, in the DNA microarray according to the present invention, the probe is preferably synthesized on a carrier based on the sequence data.

On the other hand, a method for detecting a mutation using the DNA microarray according to the present invention is a method of detecting a mutation in a genomic DNA derived from a target organism to be tested by using the aforementioned DNA microarray according to the present invention. Particularly, a mutation detection method using the DNA microarray according to the present invention includes the following steps:

extracting a genomic DNA derived from a target organism to be tested;

digesting the genomic DNA with a restriction enzyme having the same recognition sequence as the restriction enzyme used in the method for designing a probe according to the present invention;

connecting an adaptor to the genomic DNA fragments obtained by the restriction enzyme treatment;

amplifying the genomic DNA fragments using a primer capable of hybridizing to the adaptor; and detecting a hybrid of the genomic DNA fragment with the probe by bringing the amplified genomic DNA fragment into contact with the DNA microarray according to the present invention.

Herein, in the step of digesting the genomic DNA with the restriction enzyme, the genomic DNA may be digested with one or more restriction enzymes similarly to the method for designing a probe. Furthermore, in the step of connecting the adaptor, as the adaptor, one having a complementary sequence to a protruding end of the genomic DNA fragment obtained in the step of digesting the genomic DNA with the restriction enzyme is preferably used. Moreover, the step of amplifying the genomic DNA fragment may further have a step of adding a labeling molecule to an amplified genomic DNA fragment or may have a step of allowing the genomic DNA fragment to incorporate a labeling molecule when the genomic DNA fragment is amplified.

The specification of the present invention incorporates the content described in the specification and/or drawings of JP Application No. 2009-283430 A, based on which the priority of the present application is claimed.

Advantageous Effects of Invention

According to the present invention, it is possible to provide a method for designing a probe having an excellent detection rate of a polymorphism such as SNP contained in genomic DNA, for use in a DNA microarray. Furthermore, according to the present invention, it is possible to provide a DNA microarray having an excellent detection rate of a polymorphism such as an SNP contained in a genomic DNA and a method for detecting a mutation by use of the DNA microarray.

Application of the present invention enables to analyze, i.e., determine and identify, an organism species based on a genotype, although it has been difficult to detect it by a conventional method.

BRIEF DESCRIPTION OF DRAWINGS

FIG. 5 is a characteristic view showing alignment of A_1 (SEQ ID NO: 4) and A_2 (SEQ ID NO: 6), and the site of the designed probes PA_1 (nucleotides 1-60 of SEQ ID NO: 4); PA_2 (nucleotides 51-100 of SEQ ID NO: 6); PA_3 (nucleotides 101-160 of SEQ ID NO: 4); PA_4 (SEQ ID NO: 14); and PA_5 (nucleotides 202-260 of SEQ ID NO: 4).

FIG. 6 is a characteristic view showing alignment of B_1 (SEQ ID NO: 5) and B_2 (SEQ ID NO: 7), and the site of the designed probes PB_1 (nucleotides 1-70 of SEQ ID NO: 5); PB_2 (nucleotides 51-119 of SEQ ID NO: 5); PB_3 (nucleotides 101-170 of SEQ ID NO: 5); PB_4 (nucleotides 155-200 of SEQ ID NO: 5); PB_5 (nucleotides 201-252 of SEQ ID NO: 5); and PB_6 (nucleotides 251-320 of SEQ ID NO: 5).

DESCRIPTION OF EMBODIMENTS

Figure 1:
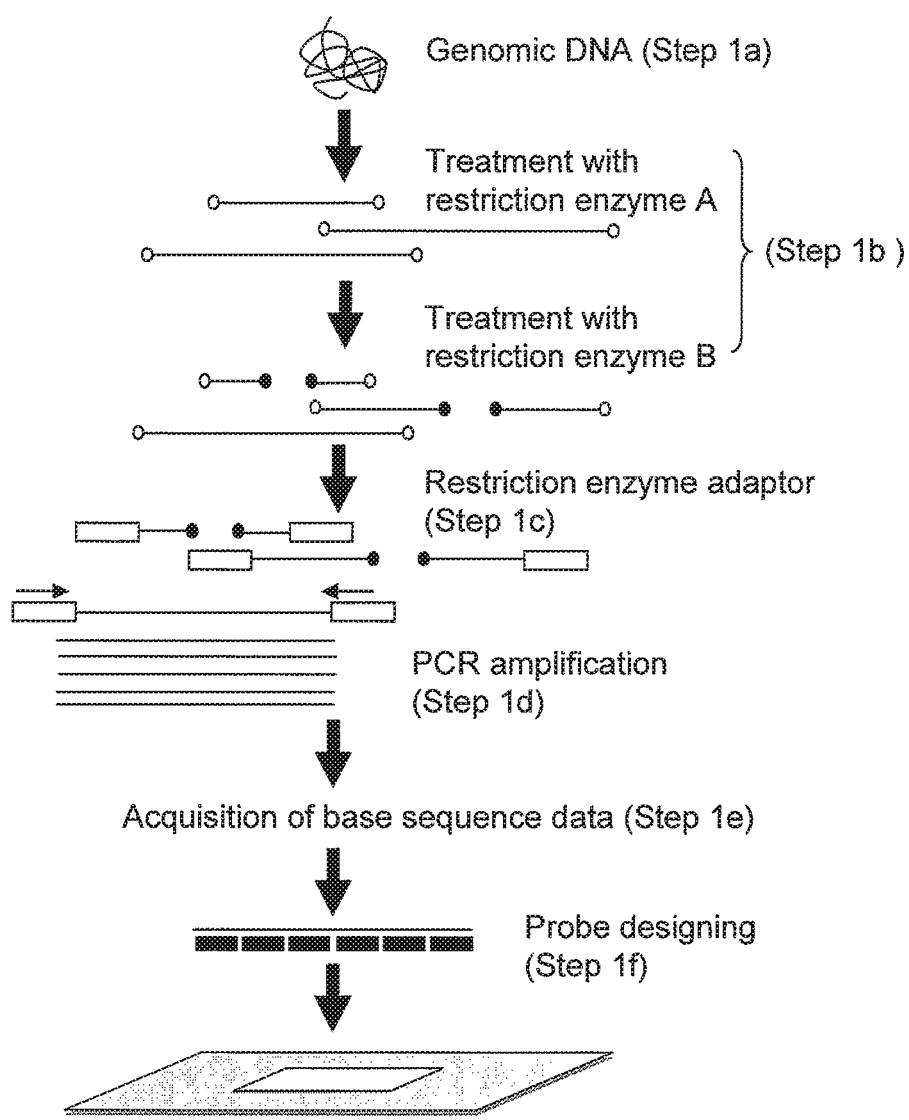
FIG. 1 is a flow chart schematically showing a method for designing a probe to which the present invention is applied.

Now, the method for designing a probe for use in the DNA microarray according to the present invention, a DNA microarray having a probe designed by the method for designing a probe, and a method of detecting a mutation by use of the DNA microarray, will be more specifically described, referring to the drawings.

Method for Designing a Probe

The probe to be designed in the present invention is preferably applied to, particularly, a so-called oligonucleotide microarray. The oligonucleotide microarray is a microarray, which is prepared by synthesizing an oligonucleotide having a desired nucleotide sequence on a carrier and using the oligonucleotide as a probe. The synthesized oligonucleotide used as a probe has, for example, a 20 to 100 nucleotide length, preferably a 30 to 90 nucleotide length, and more preferably a 50 to 75 nucleotide length.

Note that, the probe designed in the present invention may be applied to a microarray, which is prepared by spotting a synthesized oligonucleotide having the aforementioned nucleotide length onto a carrier, similarly to so-called Stanford-type microarray.

More specifically, the probe designed in the present invention can be applied to any microarray as long as it is conventionally known. Therefore, the probe designed in the present invention can be applied to a microarray using a flat substrate formed of glass and silicone etc., as a carrier and to a beads array using micro-beads as a carrier.

More specifically, in the method for designing a probe according to the present invention, first, genomic DNA is extracted from a predetermined organism, as shown in FIG. 1 (Step 1a). As the organism, any one of a microorganism such as a bacterium and a fungus, an insect, a plant and an animal may be used. Note that, the method for designing a probe shown in FIG. 1 is preferably applied to the case of using an organism whose genomic DNA nucleotide sequence data has not yet been elucidated. Furthermore, a method of extracting genomic DNA is not particularly limited and a method known in the art can be used.

Next, the extracted genomic DNA is digested with one or more restriction enzymes (Step 1b). In the example shown in FIG. 1, genomic DNA is digested with two types of restriction enzymes, restriction enzyme A and restriction enzyme B, which are sequentially used in this order. The restriction enzymes used herein are not particularly limited. For example, PstI, EcoRI, HindIII, BstNI, HpaII and HaeIII can be used. Particularly, the restriction enzyme can be appropriately selected in consideration of an appearance frequency of a recognition sequence such that genomic DNA is completely digested into genomic DNA fragments having a 20 to 10000 nucleotide length. Furthermore, in the case where more than one restriction enzyme is used, it is preferred that after all restriction enzymes are applied, the genomic DNA fragments of a 200 to 6000 nucleotide length remain. Moreover, when more than one restriction enzyme is used, the order of supplying restriction enzymes to treatment is not particularly limited. Furthermore, when common treatment conditions (solution composition, temperature etc.,) are used, more than one restriction enzyme may be used in the same reaction system. To describe more specifically, in the example shown in FIG. 1, genomic DNA is digested by using restriction enzyme A and restriction enzyme B in this order; however, restriction enzyme A and restriction enzyme B may be simultaneously used in a same reaction system to digest genomic DNA. Alternatively, restriction enzyme B and restriction enzyme A may be used in this order to digest genomic DNA. Furthermore, the number of restriction enzymes to be used may be 3 or more.

Next, to genomic DNA fragments treated by the restriction enzyme, an adaptor is connected (Step 1c). The adaptor herein is not particularly limited as long as it can connect to both ends of each of the genomic DNA fragments obtained by the aforementioned restriction enzyme treatment. As the adaptor, for example, one having a single strand complementary to a protruding end (sticky end) formed at both ends of genomic DNA fragments by restriction enzyme treatment, and having a primer binding sequence to which a primer to be used in the amplification treatment (specifically described later) can hybridize, can be used. Furthermore, as the adaptor, one having a single strand complementary to the protruding end (sticky end) and having a restriction enzyme recognition site for use in cloning into a vector.

Furthermore, in the digestion of the genomic DNA with more than one restriction enzyme, more than one adaptor can be prepared for use corresponding to the restriction enzymes. More specifically, in the digestion of the enomic DNA with more than one restriction enzyme, more than one protruding end generates. To correspond to the more than one protruding end, more than one adaptor having a single strand complementary thereto can be used. At this time, the more than one adaptor corresponding to the more than one restriction enzyme may have a common primer binding sequence such that a common primer can hybridize or may have different primer binding sequences such that different primers can hybridize.

Furthermore, in the digestion of genomic DNA with more than one restriction enzyme, an adaptor can be prepared for use corresponding to one restriction enzyme selected from the more than one restriction enzyme used or corresponding to a part of the restriction enzymes used.

Next, a genomic DNA fragment having an adaptor added to the both ends is amplified (Step 1d). When the adaptor having a primer binding sequence is used, the genomic DNA fragment can be amplified by use of a primer capable of hybridizing with the primer binding sequence. Alternatively, the genomic DNA fragment having an adaptor added thereto is cloned into a vector by use of the adaptor sequence. In this case, the genomic DNA fragment can be amplified by use of a primer capable of hybridizing to a predetermined region of the vector. Note that, as an amplification reaction of a genomic DNA fragment by use of a primer, for example, PCR can be used.

Furthermore, in the case where genomic DNA is digested with more than one restriction enzyme and more than one adaptor corresponding to the restriction enzymes are connected to the genomic DNA fragments, the adaptors will be connected to all genomic DNA fragments obtained by treatment using more than one restriction enzyme. In this case, all genomic DNA fragments obtained can be amplified by a nucleic acid amplification reaction using a primer binding sequence contained in each of the adaptors.

Alternatively, in the digestion of the genomic DNA with more than one restriction enzyme and the connection to the genomic DNA fragment an adaptor corresponding to one restriction enzyme selected from the more than one restriction enzyme used or corresponding to a part of the restriction enzymes used, only a genomic DNA fragment, of the obtained genomic DNA fragments, having a recognition sequence of the selected restriction enzyme at both ends can be amplified.

Next, the amplified genomic DNA fragment is sequenced (Step 1e), one or more regions having a shorter nucleotide length than the genomic DNA fragments and covering at least a part of the genomic DNA fragments are specified; and a probe for the one or more regions specified are designed for detecting the amplified genomic DNA fragment of an organism to be tested (Step 1f). A method for sequencing a genomic DNA fragment is not particularly limited. A method known in the art employing the Sanger method etc. and a DNA sequencer can be used.

In the steps (Steps 1e and 1f), one or more regions having a shorter nucleotide length than the amplified genomic DNA fragments are designed as a probe(s) for detecting the genomic DNA fragment. Herein, in the case where more than one region of a predetermined genomic DNA fragment are used for designing, detection of the genomic DNA fragment using more than one probe is intended. Furthermore, a single region may be selected from a genomic DNA fragment and designed, whereas a predetermined number (two or more) of regions may be selected from another genomic DNA fragment and designed. In short, the number of regions to be designed may differ from one genomic DNA fragment to another. As the regions to be designed herein, those having, for example, a 20 to 10000 nucleotide length, preferably, a 100 to 8000 nucleotide length, and more preferably, a 200 to 6000 nucleotide length are used, as mentioned above. Furthermore, in the case where more than one region is designed, the adjacent regions may be overlapped with each other or may have an interval of several nucleotides between them.

Particularly, more than one region is preferably set so as to cover the entire region of the sequenced genomic DNA fragment. In this case, more than one probe responds to a genomic DNA fragment obtained by a restriction enzyme treatment from genomic DNA derived from a predetermined organism to detect the genomic DNA fragment by these more than one probe.

Figure 2:
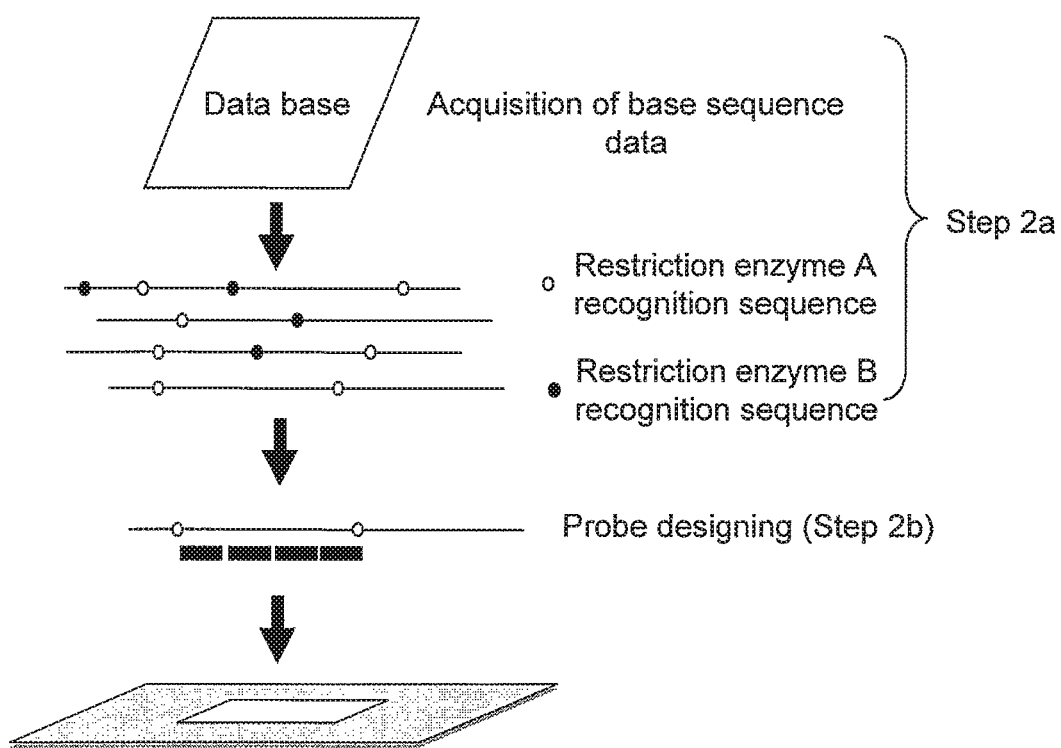
FIG. 2 is a flow chart schematically showing another method for designing a probe to which the present invention is applied.

In the meantime, the method for designing a probe according to the present invention is not limited to a method including a step of digesting genomic DNA with a restriction enzyme(s) as mentioned above, and genomic data of a target organism, as shown in FIG. 2 may be used.

In the method shown in FIG. 2, first, nucleotide sequence data on the genome derived from a target organism is obtained (Step 2a). The nucleotide sequence data on the genome can be obtained from various types of data bases known in the art. The data base is not particularly limited; however, DDBJ data base provided by the DNA Data Bank of Japan, EMBL data base provided by the European Bioinformatics Institute, Genbank data base provided by the National Center for Biotechnology Information, the KEGG data base provided by the Kyoto Encyclopedia of Genes and Genomes or data base integrated of these data bases can be appropriately used.

In this method, next, the nucleotide sequence data on the genomic DNA obtained is searched for the recognition sequence of the restriction enzyme(s) as mentioned above (Step 2a). The nucleotide sequences of genomic DNA fragments which will be obtained by digesting the aforementioned genomic DNA with the aforementioned restriction enzyme(s) are specified. The recognition sequence to be searched for herein is a restriction enzyme(s) corresponding to the restriction enzyme(s) used in the method shown in FIG. 1. More specifically, in this step, recognition sequences of one or more restriction enzymes are searched for.

Next, based on the nucleotide sequence of the determined genomic DNA fragment, one or more regions covering at least a part of the genomic DNA fragment are determined (Step 2b). In the step (Step 2b), one or more regions having a shorter nucleotide length than the sequenced genomic DNA fragments are designed as a probe for detecting the genomic DNA fragment. Herein, if more than one region is designed for a predetermined genomic DNA fragment, detection of the genomic DNA fragment using more than one probe is intended. Furthermore, a single region may be selected from a genomic DNA fragment and designed, whereas a predetermined number (2 or more) of regions may be selected from another genomic DNA fragment and designed. In short, the number of regions to be designed may differ from one genomic DNA fragment to another. As the region to be designed herein, those having, for example, a 20 to 100 nucleotide length, preferably a 30 to 90 nucleotide length, and more preferably a 50 to 75 nucleotide length are used, as mentioned above.

Furthermore, more than one region is preferably set so as to cover the entire region of the sequenced genomic DNA fragment. In this case, more than one probe responds to genomic DNA fragments obtained by a restriction enzyme treatment from genomic DNA derived from a predetermined organism to detect the genomic DNA fragment by these more than one probe.

Figure 3:
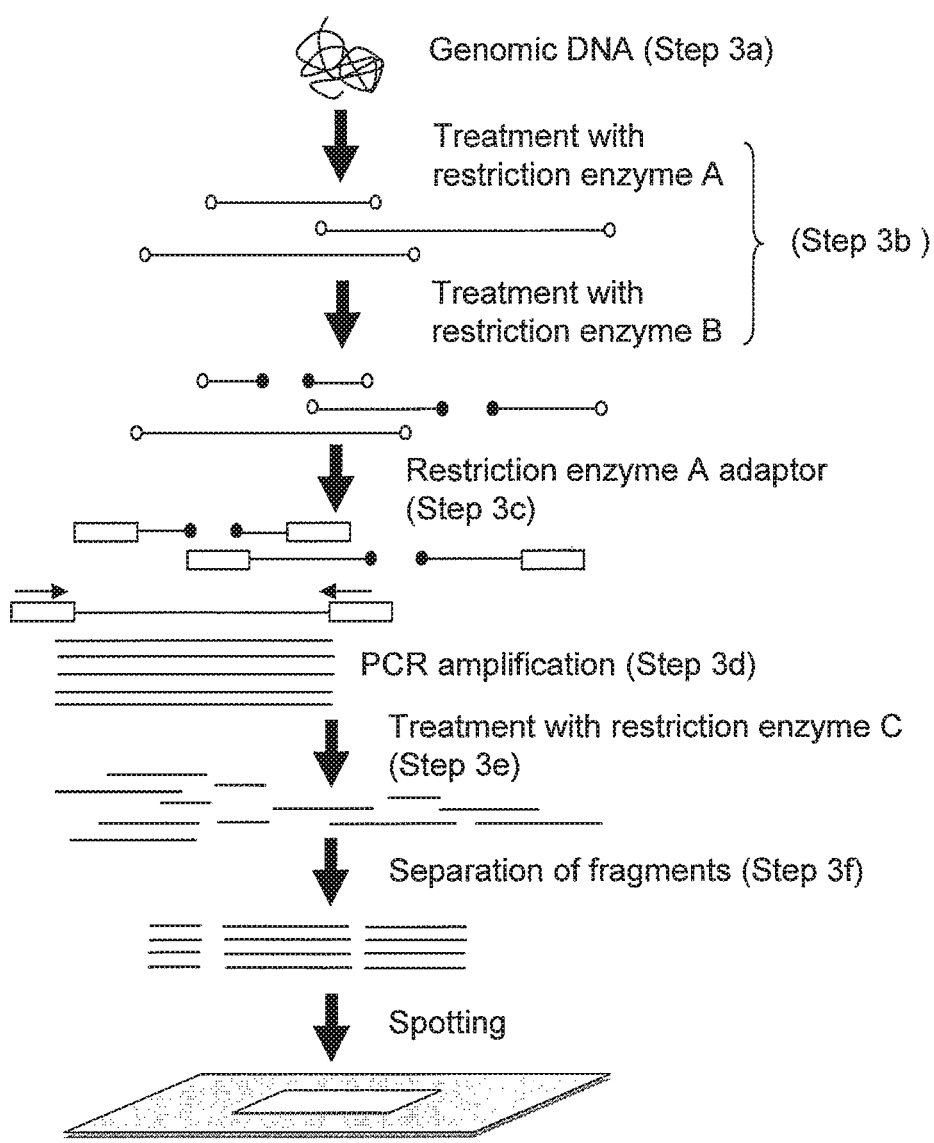
FIG. 3 is a flow chart schematically showing further another method for designing a probe to which the present invention is applied.

In the meantime, the method for designing a probe according to the present invention may be a method having neither a step of sequencing nor a step of obtaining nucleotide sequence data using a database and including a step of digesting the genomic DNA fragment with a further different restriction enzyme, as shown in FIG. 3. To describe more specifically, in the method shown in FIG. 3, first, step 1a to step 1d of the method shown in FIG. 1 are carried out to amplify a genomic DNA fragment having an adaptor attached to the both ends (Step 3a to 3d). Then, the amplified genomic DNA fragment is digested with a restriction enzyme (hereinafter, restriction enzyme C) having a different recognition sequence from the restriction enzymes used in step 3b (Step 3e). Owing to this step, the PCR fragment amplified in step 3d is digested into further shorter fragments.

In this manner, more than one region covering at least a part of the genomic DNA fragments obtained by digesting genomic DNA with restriction enzyme A and restriction enzyme B can be specified by more than one DNA fragment without sequencing. As the region to be specified, those having, for example, a 20 to 100 nucleotide length, preferably a 30 to 90 nucleotide length, and more preferably, a 50 to 75 nucleotide length are mentioned, as mentioned above. In other words, as restriction enzyme C, one capable of cleaving a genomic DNA fragment obtained by digesting genomic DNA with restriction enzyme A and restriction enzyme B into DNA fragments having, for example, a 20 to 100 nucleotide length, preferably a 30 to 90 nucleotide length, and more preferably a 50 to 75 nucleotide length can be used.

Next, the DNA fragments obtained by digestion with restriction enzyme C are separated from type to type to obtain probes (Step 3f). In this step, the DNA fragments obtained by digesting with restriction enzyme C can be separated by electrophoresis, followed by cutting out. Furthermore, the separated DNA fragment may be further cloned into a vector and used as a probe, or after cloning, may be further amplified and used as a probe. Also in this method, more than one probe responds to the genomic DNA fragments obtained in step 3d from genomic DNA derived from a predetermined organism.

DNA Microarray

The DNA microarray having a probe designed as mentioned above can be prepared by a method known in the art. For example, a DNA microarray having a probe designed by the method shown in FIG. 1 or FIG. 2 can be prepared by synthesizing an oligonucleotide having a desired nucleotide sequence on a carrier based on the nucleotide sequence of each probe designed by the method shown in FIG. 1 or FIG. 2. Herein, the method for synthesizing an oligonucleotide is not particularly limited and a method known in the art can be applied. For example, a method of synthesizing an oligonucleotide on a carrier by a photolithographic technology in combination with a light irradiation chemosynthesis technique can be applied. As another method that can be applied, an oligonucleotide having a linker molecule, which has a high affinity for a carrier surface, on an end may be separately synthesized based on the nucleotide sequence data of each probe designed by the method shown in FIG. 1 or FIG. 2, and thereafter immobilized at a predetermined position on the carrier surface.

Furthermore, the probe designed and prepared by the method shown in FIG. 3 is immobilized on a carrier to prepare a DNA microarray having a probe designed by the method shown in FIG. 3. In this case, for example, the probe designed by the method shown in FIG. 3 is spotted on a carrier by a pin type arrayer and a nozzle type arrayer to prepare a DNA microarray.

The DNA microarray prepared as described above has one or more probes having a nucleotide length shorter than the genomic DNA fragment, which is obtained by a restriction enzyme treatment of genomic DNA derived from a predetermined organism. More specifically, the DNA microarray prepared as described above is used in detecting a predetermined genomic DNA fragment by one or more probes having a nucleotide length shorter than the genomic DNA fragment. Particularly, the DNA microarray preferably has more than one probe to a predetermined genomic DNA fragment to detect the genomic DNA fragment by the more than one probe.

Note that, as the DNA microarray, any type of microarray may be used such as a microarray using a flat surface substrate formed of e.g., glass or silicone as a carrier, a beads array using micro beads as a carrier or a three dimensional microarray having a probe immobilized on the inner surface of a hollow fiber.

Method for Detecting Mutation

A mutation present in genomic DNA can be detected by using the DNA microarray prepared as described above. The mutation herein refers to a polymorphism such as a single polymorphism present between homogenous organisms, a variation of a nucleotide sequence present between related species or a mutation artificially introduced into a predetermined organism.

Figure 4:
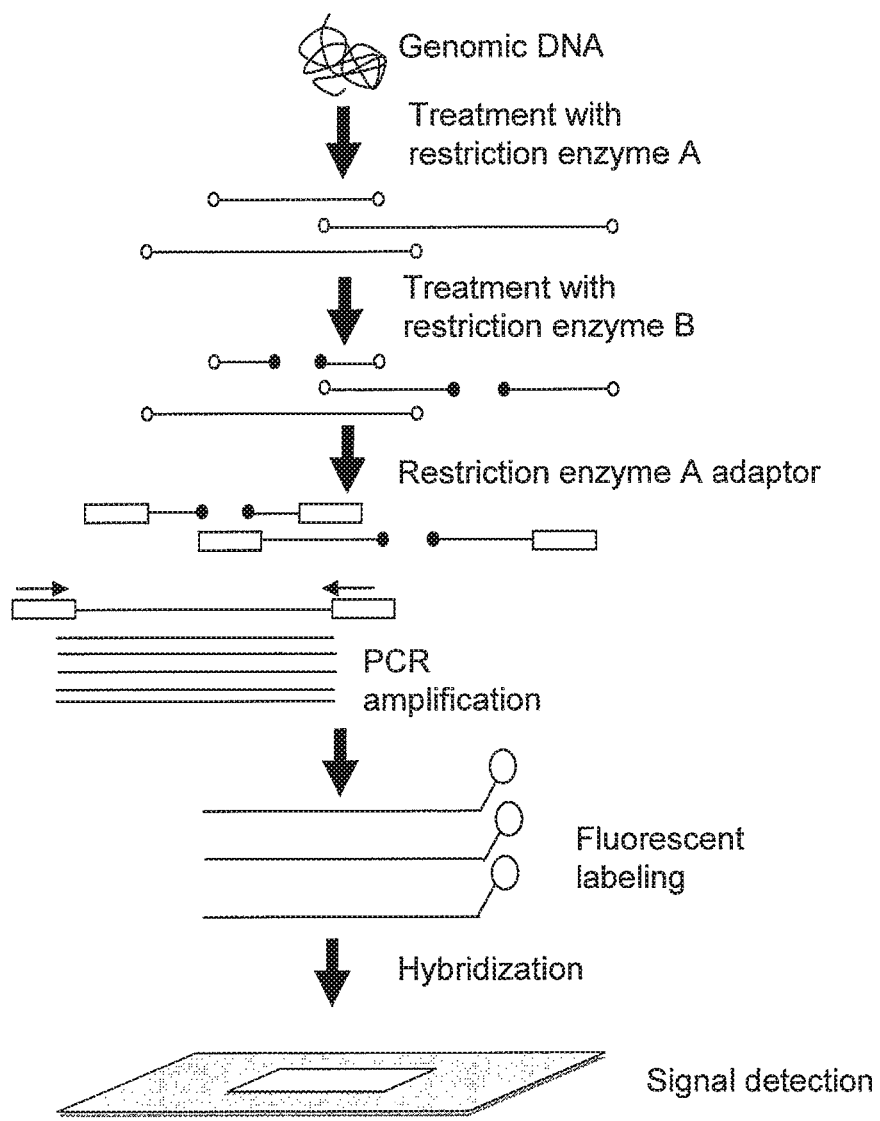
FIG. 4 is a flow chart schematically showing a step of detecting a mutation by using a DNA microarray having a probe designed by applying the present invention.

More specifically, first, a genomic DNA is extracted from an organism to be tested, as shown in FIG. 4. The organism to be tested herein is an organism to be compared to the organism used in preparing the DNA microarray. Then, the extracted genomic DNA is digested with the restriction enzyme used in preparing the DNA microarray to prepare more than one genomic DNA fragment. Subsequently, the obtained genomic DNA fragments are connected to the adaptor used in preparing the DNA microarray. Next, the genomic DNA fragment having an adaptor attached to the both ends is amplified by use of a primer used in preparing the DNA microarray. In this manner, the genomic DNA derived from an organism to be tested, which corresponds to the genomic DNA fragment amplified in step 1d for preparing the DNA microarray, the genomic DNA fragment whose nucleotide sequence is specified in step 2a, and the genomic DNA fragment amplified in step 3d, can be amplified.

In this step, of the genomic DNA fragments having an adaptor added thereto, a predetermined genomic DNA fragment may be selectively amplified. For example, in the case where more than one adaptor is used so as to correspond to more than one restriction enzyme, the genomic DNA fragment having a specific adaptor added thereto can be selectively amplified. Furthermore, of the genomic DNA fragments obtained by digesting genomic DNA with more than one restriction enzyme, only to a genomic DNA fragment having a protruding end corresponding to a predetermined restriction enzyme, an adaptor is added. In this manner, a genomic DNA fragment having the adaptor added thereto can be selectively amplified. Likewise, a predetermined genomic DNA fragment can be concentrated by selectively amplifying it.

Next, a label is added to the amplified genomic DNA fragment. As the label, any substance may be used as long as it is known in the art. As the label, for example, a fluorescent molecule, a pigment molecule and a radioactive molecule can be used. Note that, this step may be omitted by performing the step of amplifying a genomic DNA fragment by using nucleotides having a label. This is because an amplified DNA fragment is labeled by amplifying the genomic DNA fragment by use of a nucleotide having a label in above step.

Next, the genomic DNA fragment having a label is brought into contact with a DNA microarray under predetermined conditions to hybridize the probe immobilized to the DNA microarray with the genomic DNA fragment having a label. At this time, the probe partly hybridizes with the genomic DNA fragment under highly stringent conditions under which the probe does not hybridize if a single nucleotide mismatch is present but only hybridizes if the nucleotides completely match with each other. Under such highly stringent conditions thus employed, a small mutation such as a single polymorphism can be detected.

Note that, the stringent conditions can be controlled by a reaction temperature and a salt concentration. More specifically, further higher stringent conditions can be obtained by increasing the temperature and further higher stringent conditions can be obtained by reducing a salt concentration. For example, when a probe having a 50 to 75 nucleotide length is used, further higher stringent conditions are prepared if conditions of 40 to 44° C., 0.21 SDS, 6×SSC are employed.

Furthermore, hybridization between the probe and the genomic DNA fragment having a label can be detected based on the label. More specifically after a hybridization reaction between the aforementioned genomic DNA fragment having a label and a probe, unreacted genomic DNA fragments etc. were washed away. Thereafter, the label of the genomic DNA fragment specifically hybridized to the probe is observed. For example, in the case where the label is a fluorescent substance, the fluorescent wavelength is detected. In the case where the label is a pigment molecule, the wavelength of the pigment is detected. More specifically, a fluorescent detection apparatus and an image analyzer etc., usually used for DNA microarray analysis, can be used.

Figure 9:
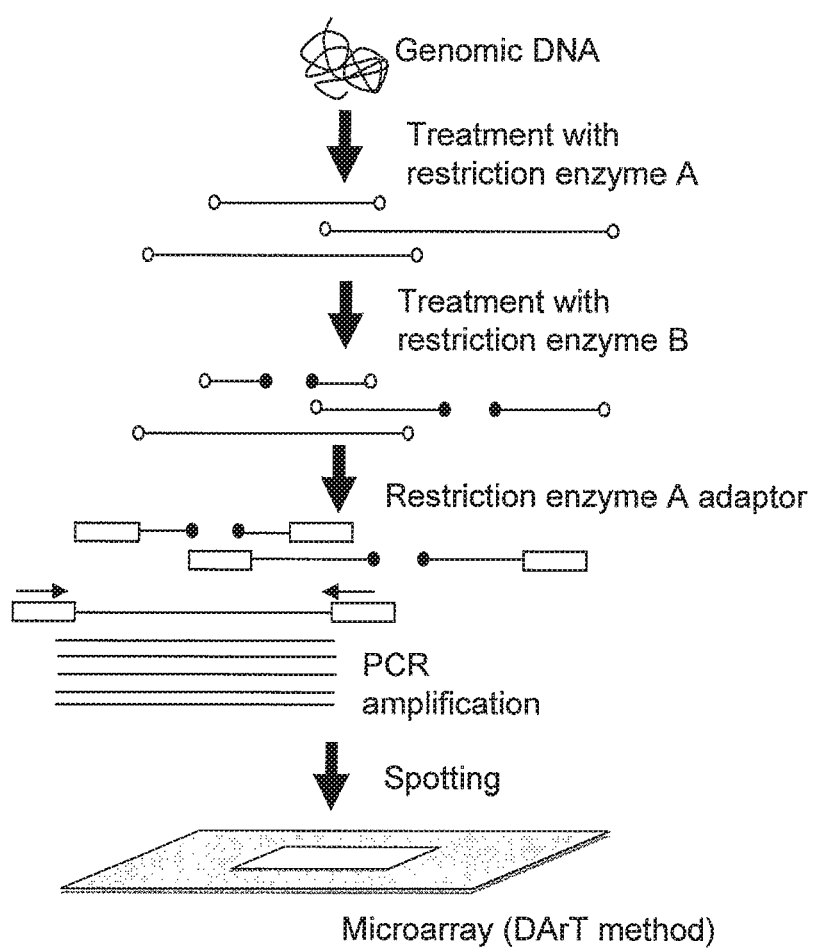
FIG. 9 is a characteristic view schematically showing a step of preparing a DNA microarray used in a conventional DArT method.

Particularly, if the aforementioned DNA microarray is used, the genomic DNA fragment derived from an organism to be tested is detected by one or more probes having a shorter nucleotide length than the genomic DNA fragments. In a conventional DArT method (FIG. 9), since a genomic DNA fragment derived from a predetermined organism is amplified by PCR and used as a probe, even if a genomic DNA fragment derived from an organism to be tested having a mismatch of several tens of nucleotides, the probe often hybridized with it (pseudo-positive reaction). However, in the aforementioned DNA microarray, since detection was made by use of one or more probes having a shorter nucleotide length than the genomic DNA fragments, an incident probability of such a pseudo-positive reaction can be reduced, with the result that a genomic DNA fragment derived from an organism to be tested can be highly accurately detected. Particularly, when a genomic DNA fragment derived from an organism to be tested is detected by more than one probe, a small mutation contained in a genomic DNA fragment derived from an organism to be tested can be detected by detecting the presence or absence of hybridization in more than one probe.

Furthermore, in the aforementioned DNA microarray, an unknown mutation can be detected. In a conventional DNA microarray using an oligonucleotide synthesized on a carrier as a probe for mutation detection, a detection target is only a known mutation having known sequence data. However, according to the aforementioned method for designing a probe, even if a genomic DNA fragment contains a mutation whose sequence has not yet been found, such an unknown mutation can be a target of detection. In other words, an unknown mutation can be found by use of the DNA microarray having the aforementioned probe.

As described in the foregoing, according to the DNA microarray of the present invention, since a mutation contained in the genomic DNA of an organism to be tested can be detected in comparison with that of a predetermined organism used in preparing the DNA microarray, for example, diversity in homogeneous organisms can be analyzed at a gene level. Furthermore, if the DNA microarray according to the present invention is prepared with respect to various types of variants contained in homogenous organism, which variant an organism to be tested belongs to can be analyzed at a gene level.

EXAMPLES

Now, the present invention will be more specifically described by way of Examples. The technical range of the present invention is not limited by the following Examples.

Example 1

In this Example, it was shown that a mutation present in an allele of each of sugar cane varieties NiF8 and Ni9 can be detected by designing a probe in accordance with the procedure shown in FIG. 1 without using the whole sequence data or mutation data.

(1) Material

Sugar cane varieties NiF8 and Ni9 were used.

(2) Treatment with Restriction Enzyme

Genomic DNA was extracted separately from sugar cane varieties NiF8 and Ni9 in accordance with a customary method. Genomic DNA (750 ng) was treated with restriction enzyme PstI (NEB Inc. 25 units) at 37° C. for 2 hours, followed with restriction enzyme BstNI (NEB Inc., 25 units) at 60° C. for 2 hours.

(3) Adaptor Ligation

To the genomic DNA fragment (120 ng) treated in the step (2), PstI sequence adaptors (5'-CACGATGGATCCAGT-GCA-3' (SEQ ID NO: 1), 5'-CTGGATCCATCGTGCA-3' (SEQ ID NO: 2)) and T4 DNA Ligase (NEB Inc., 800 units) were added and a treatment was performed at 16° C., all night and all day. In this manner, the adaptor was selectively added to the genomic DNA fragment having a PstI recognition sequence at the both ends, among those treated in the step (2).

(4) PCR Amplification

To the genomic DNA fragments (15 ng) having an adaptor obtained in the step (3), a PstI sequence adaptor recognizing primer (5'-GATGGATCCAGTGCAG-3' (SEQ ID NO: 3)) and Taq polymerase (company TAKALA, PrimeSTAR, 1.25 units) were added and genomic DNA fragments were amplified by PCR (a cycle consisting of 10 seconds at 98° C., 15 seconds at 55° C., and 1 minute at 72° C. was repeated 30 times and the PCR sample was treated at 72° C. for 3 minutes and stored at 4° C.).

(5) Acquisition of Genomic Sequence

The genomic DNA fragment amplified by PCR in the step (4) was analyzed by the Sanger method for sequencing. As a result, 2 types of genomic sequence data (A_1 (SEQ ID NO: 4) and B_1 (SEQ ID NO: 5)) derived from NiF8 were obtained. Furthermore, genomic sequence data (A_2 (SEQ ID NO: 6) and B_2 (SEQ ID NO: 7)) of locus region of Ni9 allele were obtained by use of sequence data of genomic sequence A_1 and B_1.

(6) Probe Designing

Based on the genomic sequence data (A_1, B_1) of the step (5), 5 and 6 probes of a 50 to 70 bp were separately designed. More specifically, in this Example, a probe of sugar cane variety NiF8 was designed. A_1 and A_2 alignments and the position of the designed probe are shown in FIG. 5. Furthermore, B_1 and B_2 alignments and the position of the designed probe are shown in FIG. 6.

(7) Preparation of Array

Based on the nucleotide sequence data of the designed probes, the DNA microarrays having these probes were prepared (outsource to Roche).

(8) Sample Preparation

Fragments from sugar cane varieties NiF8 and Ni9 were separately amplified by PCR in accordance with the aforementioned methods (2) to (4). PCR amplification fragments were purified by a column (company, Qiagen), and thereafter, Cy3-labeled 9mers (TriLink Inc., 1O.D.) was added. The mixture was treated at 98° C. for 10 minutes and allowed to stand still on ice for 10 minutes. Thereafter, Klenow (NEB Inc., 100 units) was added. The mixture was treated at 37° C. for 2 hours and then precipitated with ethanol to prepare a labeled sample.

(9) Detection of Hybridization Signal

Hybridization was performed by use of the DNA microarray prepared in the step (7) and using the labeled sample of the step (8) in accordance with the NimbleGen Array User's Guide to detect a signal derived from the label.

(10) Calculation of Mutation Rate

A mutation rate was calculated based on homology of the genome sequence of the loci regions of NiF8 and Ni9 alleles within respective probes.

(11) Calculation of Signal Intensity Ratio

The signal intensity ratio is obtained by dividing the signal intensity of array using NiF8 as a sample by the signal intensity of the array using Ni9 as a sample.

(12) Results and Discussion

The measurement results of signal intensity and the signal intensity ratio calculated from the results are shown in Table 1 and Table 2.

TABLE 1

|  | probe length (bp) | Mutation rate (%) | Signal intensity | | signal intensity ratio |
|---|---|---|---|---|---|
|  |  |  | NiF8 | Ni9 |  |
| PA_1 | 60 | 91.7% | 2,304 | 225 | 10.2 |
| PA_2 | 50 | 54.0% | 1,318 | 249 | 5.3 |
| PA_3 | 65 | 0.0% | 4,837 | 4,554 | 1.1 |
| PA_4 | 58 | 3.4% | 1,738 | 894 | 1.9 |
| PA_5 | 60 | 0.0% | 4,240 | 3,075 | 1.4 |

TABLE 2

|  | Probe length (bp) | Mutation rate (%) | Signal intensity | | Signal intensity ratio |
|---|---|---|---|---|---|
|  |  |  | NiF8 | Ni9 |  |
| PB_1 | 69 | 4.3% | 1,921 | 298 | 6.4 |
| PB_2 | 69 | 10.1% | 3,398 | 272 | 12.5 |
| PB_3 | 70 | 5.7% | 541 | 247 | 2.2 |
| PB_4 | 50 | 30.0% | 608 | 209 | 2.9 |
| PB_5 | 52 | 1.9% | 1,463 | 902 | 1.6 |
| PB_6 | 70 | 1.4% | 2,807 | 2,665 | 1.1 |

From FIG. 5, it was found that a single insertion/deletion mutation of 101 bp and three mutations of 1 to several-bases mutation are present between A_1 and A_2. From Table 1, it was found that, in a probe (PA_3 and PA 5, mutation rate 0%) having no mutation between NiF8 and Ni9, high signal intensity was detected in each of NiF8 and Ni9. This means that A_1 and A_2 sequences corresponding to the sequence data are present respectively in the samples of NiF8 and Ni9. Furthermore, since the signal intensity ratio of both samples is as low as 1.1 to 1.4, signal intensity ratio of a probe having no mutation was low.

On the other hand, as a mutation rate increases, the signal intensity ratio of both samples increased (1.9 (PA_4) to 10.2 (PA_1)). This is because, A_2 sequence is present in the Ni9 sample but a mutation is present in A_2 sequence, which corresponds to PA_1, PA_2, and PA_4 probes, with the result that hybridization strength decreases and the signal of Ni9 decreases.

Similarly, from FIG. 6, it is found that three insertion/deletion mutations and 14 SNPs are present between B_1 and B_2. Also with respect to B_1 and B_2, a signal intensity ratio increases as a mutation rate increases (1.1 (PB_6) to 12.5 (PB_2)) as is apparent from Table 2.

From the above results, it was demonstrated that DNA mutation of a several-bp level can be detected and the site of a mutation of several-tens of nucleotides can be specified by using a probe having a nucleotide length shorter than a genomic DNA fragment serving as a sample.

Example 2

In this Example, to the probe derived from NiF8 prepared in Example 1, a mutation was artificially introduced. Based on the mutation introduction rate and the signal intensity ratio thereof to an original probe, the mutation detection ability was evaluated.

(1) Material

Sugar cane variety NiF8 was used.

(2) Acquisition of Basic Probe Sequence Data

A PCR amplification fragment of NiF8 was prepared in accordance with the steps (2) to (4) of Example 1 and the genomic sequence was determined by the Sanger method. Based on independent genomic sequence data, 6 basic probes having a 50 to 75 bp were prepared (Table 3).

TABLE 3

| Probe | Sequence | Sequence length |
|---|---|---|
| PC_1 | gccgtcgctcacaaggaccaacg aacggaaaggcatgcatgcagag agtt (SEQ ID NO: 8) | 64 |
| PC_2 | tatgagctatatgtaatgtaagt gtactactctcctgtcaccttgc acttgacagca (SEQ ID NO: 9) | 71 |
| PC_3 | cctctctttgctccgaaattggt catgtactcatgttatatgcaat atatacggagtagtact (SEQ ID NO: 10) | 78 |
| PC_4 | tcagaaacgcaacattctgcact ctgattttactatatgcatcgct tctcattttactgacttg (SEQ ID NO: 11) | 79 |
| PC_5 | aagtaatgttatcaatcggcaaa tcaaatatggccagaatcaacat aagaaactgagatttggcacaga aatg (SEQ ID NO: 12) | 88 |
| PC_6 | ttcatctacatttagtactccat gcatatatcgcaagtttgatgtg acggaaatcttttgtttgcacaa tacttt (SEQ ID NO: 13) | 90 |

(3) Preparation of Mutation Probe

Probes were prepared by separately inserting, deleting and substituting with 1, 2, 3, 4, 5, 10, 15, 20 and 25 nucleotides into, from and for the basic probes of the step (2).

(4) Array Preparation, Labeling, Hybridization-Signal Detection

A DNA microarray was prepared in the same manner as in the steps (7) to (9) of Example 1. A sample was prepared and a hybridization reaction and the following signal detection were performed.

(5) Calculation of Signal Intensity Ratio

The value of the signal intensity ratio was obtained by dividing the signal intensity of a mutation probe by the basic probe signal intensity. A graph and an approximation curve were prepared by Excel 2007.

(6) Results and Discussion

Figure 7:
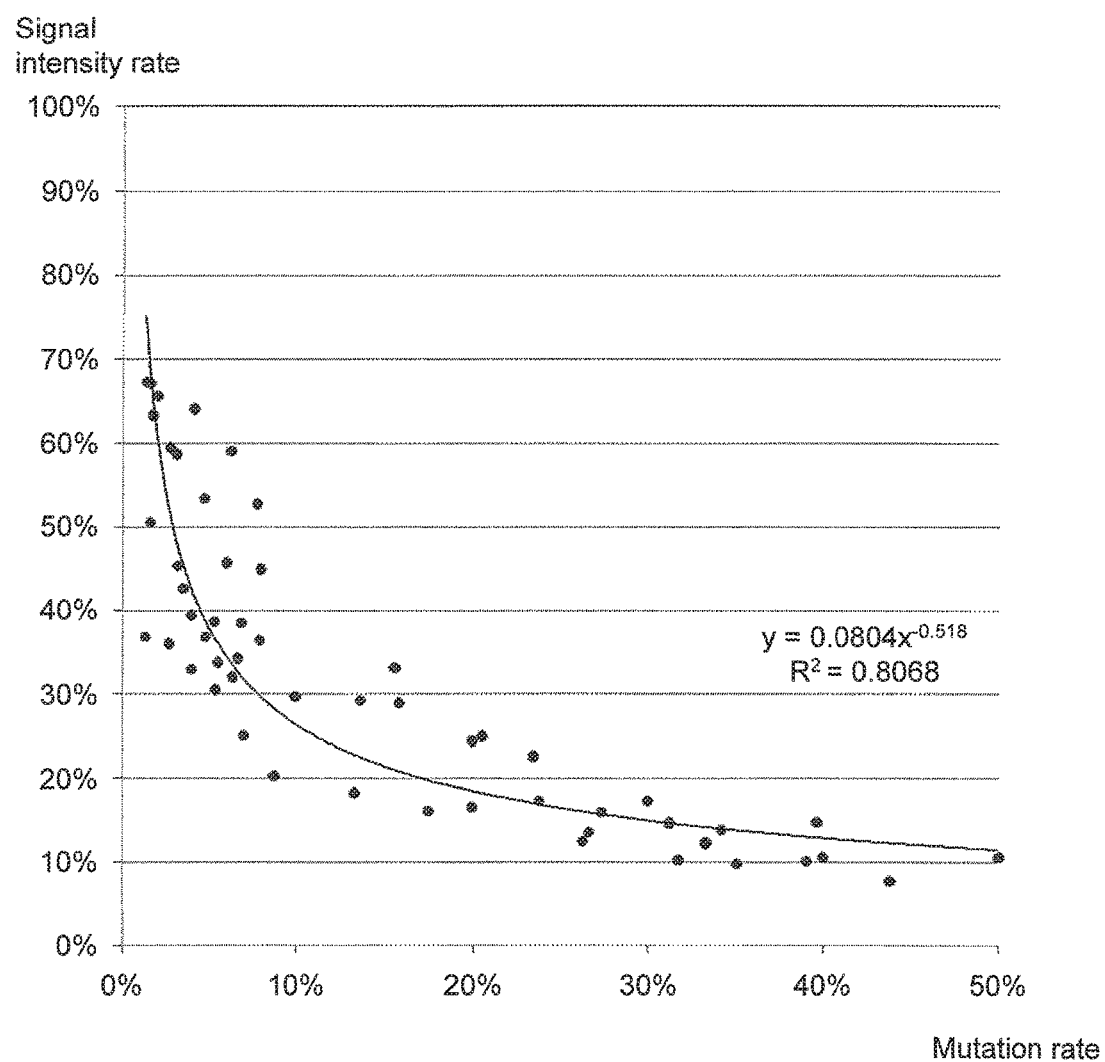
FIG. 7 is a characteristic graph showing the relationship between the rate of mutation introduced in a probe and the intensity of a signal detected.

The relationship between the mutation rate introduced into a probe and the signal intensity detected is shown in FIG. 7. As shown in FIG. 7, the mutation rate of a probe and the signal intensity ratio are highly correlated (y=0.0804x− 0.518, R2=0.8068). From the correlation, it was found that a signal intensity ratio tends to reduce to 50% or less at a mutation rate of 3% or more. Even if there is a 1 bp mutation, the signal intensity ratio decreases up to less than 50% depending upon the probe. From the above results, it was demonstrated that mutation of a single to several nucleotides or more can be highly accurately detected by a probe having a nucleotide length shorter than the genomic DNA fragment.

Example 3

In this Example, using sugar cane varieties NiF8 and Ni9 genomic sequence data (5,848 nucleotides), 5 to 15 probes consisting of several tens of bps were prepared for each genomic sequence datum and detection of a mutation between both samples was carried out.

(1) Material

Sugar cane varieties NiF8 and Ni9 were used.

(2) Acquisition of Genomic Sequence Data

Fragments of NiF8 and Ni9 were amplified by PCR according to the steps (2) to (4) of Example 1 and analyzed by the Sanger method to obtain the genomic sequence data. More specifically genomic sequence data of 5,848 PCR amplification fragments were obtained.

(3) Preparation of Probe

Five to fifteen probes each having 50 to 75 bp were designed based on the genomic sequence data obtained in the step (2). More specifically, based on the genomic sequence data (5,848 data), 59,462 probes were designed.

(4) Array Preparation, Labeling, Hybridization-Signal Detection

A DNA microarray was prepared in accordance with the steps (7) to (9) of Example 1. A sample was prepared and a hybridization reaction and the following signal detection were performed (5) Detection of Mutation-Site Probe When a signal intensity ratio of an array using Ni9 as a sample to an array using NiF8 as a sample is twice or more or ½ or less, the probe was determined as a mutation-site probe.

(6) Ratio of Mutation-Site Probe Per Sequence Data

A value obtained by dividing the number of mutation-site probes per sequence datum by the number of probes prepared per sequence datum, was used.

Figure 8:
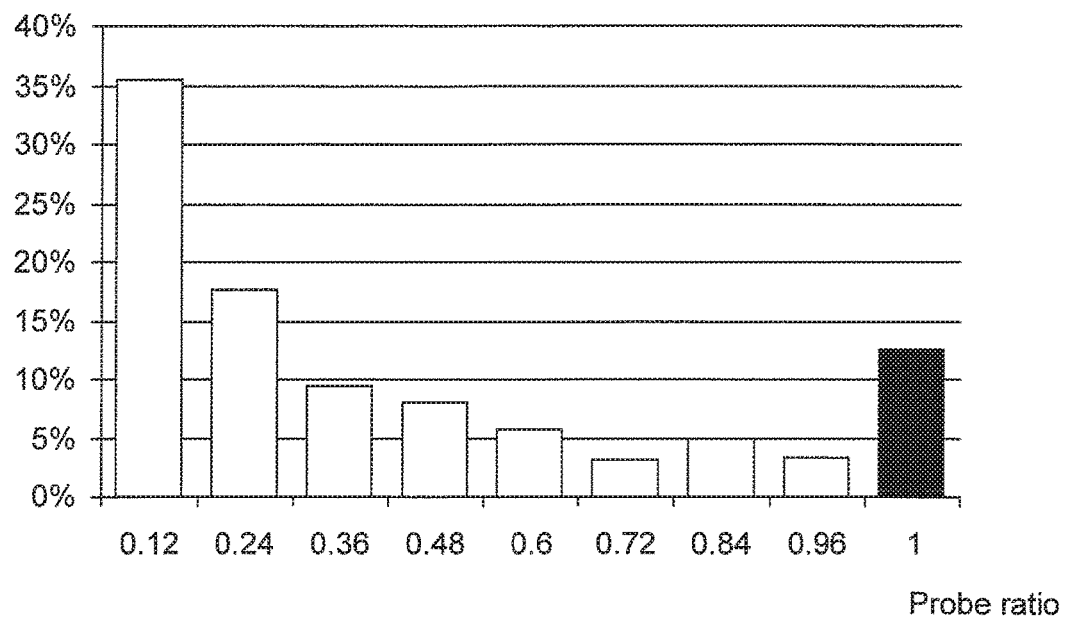
FIG. 8 is a characteristic graph showing the relationship between the ratio of mutation site probe prepared in Example 3 and the ratio of the sequence data in which a mutation was detected.

(7) Results and Discussion 59,462 probes were designed from 5,848 genomic sequence data. Of them, the number of probes in the case where a signal intensity ratio was beyond 2, was 5,596. Sequence data having at least one of such a probe was 1,497. Of these sequence data, the number of data providing a signal intensity ratio of 2 or more in all probes were 189, which was 12.6% of the total (FIG. 8). It was considered that mutation within the sequence data is caused by a large insertion/deletion of several kbp within a restriction enzyme recognition sequence. On the other hand, the sequence data in which a mutation was detected in a part of probes was 87.4% of all data. This is because an ability to detect a mutation is improved by designing more than one probe of several tens of bps in the interior. From the above results, in all probes, the sequence data in which a mutation of this time was detected is 7.9 fold as large as the sequence data providing a signal intensity ratio of 2 fold or more. Thus, it was clearly demonstrated that the ability to detect a mutation improves by designing more than one probe having several tens of bps, which is shorter than a genomic DNA fragment serving as a sample.

Example 4

In this Example, to validate availability of a DNA microarray having a probe designed based on known sequence data of another organism, a DNA microarray having a probe designed based on the total sequence data of Sorghum was prepared and a mutation of sugar cane genomic DNA was detected.

(1) Material

Sugar cane varieties NiF8 and Ni9 were used.

(2) Acquisition of Sorghum Genomic Sequence Data from Genome DB

From Sorghum total genomic sequence data of genome DB (Gramene: http://www.gramene.org/), sequence data between PstI recognition sequences were obtained.

(3) Preparation of Probe

Based on the sequence data of step (2), a probe having 50 to 75 bp was designed.

(4) Array Preparation, Labeling, Hybridization-Signal Detection

A DNA microarray was prepared in accordance with the steps (7) to (9) of Example 1. A sample was prepared and a hybridization reaction and the following signal detection were performed.

(5) Calculation of the Number of Mutation-Site Probes

When a signal intensity ratio of an array using Ni9 as a sample to an array using NiF8 as a sample is twice or more or ½ or less, the probe was determined as a mutation-site probe.

(6) Results and Discussion

In this Example, 1,744,104 probes were designed based on Sorghum genomic sequence data, as shown in Table 4.

TABLE 4

| | Number of probes | | |
| --- | --- | --- | --- |
| Chromosome | Total number of test samples | Signal (1,000 or more) | Detection number of mutations |
| Chr.1 | 215,534 | 14,988 | 3,959 |
| Chr.2 | 191,280 | 12,627 | 3,383 |
| Chr.3 | 214,387 | 13,138 | 3,629 |
| Chr.4 | 183,499 | 10,658 | 2,794 |
| Chr.5 | 161,513 | 6,810 | 1,952 |
| Chr.6 | 164,830 | 8,830 | 2,330 |
| Chr.7 | 161,463 | 6,846 | 1,959 |
| Chr.8 | 138,922 | 5,819 | 1,656 |
| Chr.9 | 153,484 | 7,426 | 1,930 |
| Chr.10 | 159,192 | 8,278 | 2,155 |
| All | 1,744,104 | 95,420 | 25,747 |

Of them, the number of sequence data having a probe providing a signal intensity of 1,000 or more was 95,420. The ratio of this to the number of sequence data used was 4.2% to 7.0% per Sorghum chromosome. In total, it was 5.5%. From the results, it was considered that a homologous region to these probe sequences is present each in sugar cane NiF8 and Ni9. Furthermore, of these probes, the number of probes in the case where a signal intensity ratio was beyond 2, in NiF8 and Ni9, was 25,747. It was 1.2% to 1.8% per chromosome of the test probes. In total, it was 1.5%. In the region of a probe providing a signal intensity ratio exceeding 2, it is considered that a mutation is present between NIF8 and Ni9. From the results in the foregoing, it is clearly demonstrated that designing a probe by use of genome information of another organism can be used for analyzing gene mutation in a predetermined organism.

All publications and patents and patent applications cited in the specification are incorporated by reference in its entirety.

The invention claimed is:

1. A method for detecting a mutation using a DNA microarray having a plurality of polynucleotide probes immobilized thereon, said method comprising the steps of:
   extracting a genomic DNA derived from an organism to be tested;
   digesting the genomic DNA with a restriction enzyme having the same recognition sequence as a restriction enzyme used to design the probes immobilized on the DNA microarray;
   connecting an adaptor to the genomic DNA fragments obtained by the restriction enzyme treatment;
   amplifying the genomic DNA fragments using a primer capable of hybridizing to the adaptor; and
   detecting a hybrid of a genomic DNA fragment containing a mutation with a probe capable of detecting the mutation, by bringing the amplified genomic DNA fragment into contact with the DNA microarray,
   wherein said DNA microarray comprises a plurality of probes, and a carrier on which the probes are immobilized, wherein said plurality of probes is capable of detecting a mutation contained in a genomic DNA fragment obtained by said digesting, wherein the plurality of polynucleotide probes comprises probes covering different portions of the genomic DNA fragment, wherein the plurality of polynucleotide probes covers the entire region of the genomic DNA fragment, and wherein the probes in said plurality of polynucleotide probes are shorter in length than the genomic DNA fragment.

2. The method according to claim 1, wherein, in the step of digesting the genomic DNA, the genomic DNA is digested with a plurality of restriction enzymes.

3. The method according to claim 2, wherein, in the connecting step, an adaptor is connected which corresponds to one restriction enzyme from said plurality of restriction enzymes, or which corresponds to several of the restriction enzymes in said plurality of restriction enzymes.

4. The method according to claim 1, wherein the adaptor has a complementary sequence to a protruding end of the genomic DNA fragments obtained in the step of digesting the genomic DNA with a restriction enzyme.

5. The method according to claim 1, wherein the organism to be tested is different from the organism used in preparing the DNA microarray.

* * * * *

SEQUENCE LISTING

<160> NUMBER OF SEQ ID NOS: 14

<210> SEQ ID NO 1
<211> LENGTH: 18
<212> TYPE: DNA
<213> ORGANISM: Artificial Sequence
<220> FEATURE:
<223> OTHER INFORMATION: Synthetic DNA

<400> SEQUENCE: 1
cacgatggat ccagtgca                                                   18

<210> SEQ ID NO 2
<211> LENGTH: 16
<212> TYPE: DNA
<213> ORGANISM: Artificial Sequence
<220> FEATURE:
<223> OTHER INFORMATION: Synthetic DNA

<400> SEQUENCE: 2
ctggatccat cgtgca                                                     16

<210> SEQ ID NO 3
<211> LENGTH: 16
<212> TYPE: DNA
<213> ORGANISM: Artificial Sequence
<220> FEATURE:
<223> OTHER INFORMATION: Synthetic DNA

<400> SEQUENCE: 3
gatggatcca gtgcag                                                     16

<210> SEQ ID NO 4
<211> LENGTH: 260
<212> TYPE: DNA
<213> ORGANISM: Saccharum officinarum

<400> SEQUENCE: 4
aatacccctc tctaggcttt ggaattgtgc tgtgatgata aaatgaatgt gatgcaaatg      60
ctcatgcttt ggaattagag cctttcagtc ctgagctagg taggctttac tagctgttat     120
tgtttctttc ctattgctta tttcgagacc agtatcccta agagtggcat ttttttttctg    180 cccctaagag agtacattca tgtgtcttgt gatgtaacaa atcacgtgtt ccttcgctaa     240
aataaatatg catggtcctc                                                260

<210> SEQ ID NO 5
<211> LENGTH: 320
<212> TYPE: DNA
<213> ORGANISM: Saccharum officinarum

<400> SEQUENCE: 5
acccgttatt atcatatgtt tactgtagca caatattgtc taattacgga ctgattaggc      60
tcaaaaaaat catctcgcaa aatatacgca atttgtgtaa ttaattatttt tttagtctac    120 atttaatact tcatatgtgt gtcaaacatc cgatgtgata gggtaggga gaaactaaaa      180 gtcccaccat tatttcgtac cagtgaagct gacgcatctt aattgcttct gaccaaatgt     240
ttagtagcag cagtactatc atattcttcc tgctgctcat aatatgattt tgtcttgcat     300
attttcagga gactactgag                                                320

<210> SEQ ID NO 6
<211> LENGTH: 192

<212> TYPE: DNA
<213> ORGANISM: Saccharum officinarum

<400> SEQUENCE: 6

```
aatatctggg agcctttcag tcctgagcta ggtaggcttt actagctgtt attgtttctt     60
tcctattgct tatttcgaga ccagtatccc taagagtggc attttttgc tgcccctaag    120
agagcacatt catgtgtctt gtgatgtaac aaatcacgtg ttccttcgct aaaataaata   180
tgcatggtcc tc                                                        192
```

<210> SEQ ID NO 7
<211> LENGTH: 331
<212> TYPE: DNA
<213> ORGANISM: Saccharum officinarum

<400> SEQUENCE: 7

```
acctgttatt atcatatgtt tactgtagca caacattgtc taattacgga ctaattaggc     60
tcaaaaaaat cgtctagcaa aatacacgca atctgtgcaa ttaattattt ttttagtcta    120
catttaatac ttcatacgtg tatcaaacat ccgatgtgat agggtagagg aggaactaaa   180
caagtccttta gttgccagca ttatttcgta ccagtgaagc tgatgcatct taattgcttc  240
tgaccaaatg tttagtagca gcagtactat catattcttc ctgctactca taatatgatt  300
ttgtcttgca tattttcagg agactactga g                                   331
```

<210> SEQ ID NO 8
<211> LENGTH: 50
<212> TYPE: DNA
<213> ORGANISM: Artificial Sequence
<220> FEATURE:
<223> OTHER INFORMATION: Synthetic DNA

<400> SEQUENCE: 8

```
gccgtcgctc acaaggacca acgaacggaa aggcatgcat gcagagagtt                50
```

<210> SEQ ID NO 9
<211> LENGTH: 57
<212> TYPE: DNA
<213> ORGANISM: Artificial Sequence
<220> FEATURE:
<223> OTHER INFORMATION: Synthetic DNA

<400> SEQUENCE: 9

```
tatgagctat atgtaatgta agtgtactac tctcctgtca ccttgcactt gacagca       57
```

<210> SEQ ID NO 10
<211> LENGTH: 63
<212> TYPE: DNA
<213> ORGANISM: Artificial Sequence
<220> FEATURE:
<223> OTHER INFORMATION: Synthetic DNA

<400> SEQUENCE: 10

```
cctctctttg ctccgaaatt ggtcatgtac tcatgttata tgcaatatat acggagtagt    60
act                                                                  63
```

<210> SEQ ID NO 11
<211> LENGTH: 64
<212> TYPE: DNA
<213> ORGANISM: Artificial Sequence
<220> FEATURE:
<223> OTHER INFORMATION: Synthetic DNA
```

```
<400> SEQUENCE: 11
tcagaaacgc aacattctgc actctgattt tactatatgc atcgcttctc attttactga      60
cttg                                                                  64

<210> SEQ ID NO 12
<211> LENGTH: 73
<212> TYPE: DNA
<213> ORGANISM: Artificial Sequence
<220> FEATURE:
<223> OTHER INFORMATION: Synthetic DNA

<400> SEQUENCE: 12
aagtaatgtt atcaatcggc aaatcaaata tggccagaat caacataaga aactgagatt      60
tggcacagaa atg                                                        73

<210> SEQ ID NO 13
<211> LENGTH: 75
<212> TYPE: DNA
<213> ORGANISM: Artificial Sequence
<220> FEATURE:
<223> OTHER INFORMATION: Synthetic DNA

<400> SEQUENCE: 13
ttcatctaca tttagtactc catgcatata tcgcaagttt gatgtgacgg aaatcttttg      60
tttgcacaat acttt                                                      75

<210> SEQ ID NO 14
<211> LENGTH: 58
<212> TYPE: DNA
<213> ORGANISM: Artificial Sequence
<220> FEATURE:
<223> OTHER INFORMATION: Synthetic DNA

<400> SEQUENCE: 14
agtatcccta agagtggcat tttttgctg cccctaagag agtacattca tgtgtctt        58
```